United States Patent [19]
Hauptman

[11] Patent Number: 6,147,108
[45] Date of Patent: Nov. 14, 2000

[54] METHOD FOR TREATING TYPE II DIABETES MELLITUS

[75] Inventor: Jonathan Brian Hauptman, Ridgewood, N.J.

[73] Assignee: Hoffman-La Roche Inc., Nutley, N.J.

[21] Appl. No.: 09/411,554

[22] Filed: Oct. 4, 1999

Related U.S. Application Data

[63] Continuation of application No. 09/262,564, Mar. 4, 1999, which is a continuation of application No. 09/003,138, Jan. 6, 1998.
[60] Provisional application No. 60/037,383, Feb. 5, 1997, abandoned.
[51] Int. Cl.[7] .................. A61K 31/365; A61K 31/35; A61K 9/16
[52] U.S. Cl. .................. 514/449; 549/263; 549/292; 549/328; 514/866; 514/909
[58] Field of Search .................. 514/449, 866, 514/909

[56] References Cited

U.S. PATENT DOCUMENTS

| | | |
|---|---|---|
| 4,598,089 | 7/1986 | Hadvary et al. . |
| 4,983,746 | 1/1991 | Barbier et al. . |
| 5,130,333 | 7/1992 | Pan et al. . |
| 5,175,186 | 12/1992 | Barbier et al. . |
| 5,190,970 | 3/1993 | Pan et al. . |
| 5,298,497 | 3/1994 | Schollar et al. . |
| 5,345,056 | 9/1994 | Karpf et al. . |
| 5,399,720 | 3/1995 | Karpf et al. . |
| 5,447,953 | 9/1995 | Isler et al. . |
| 5,461,039 | 10/1995 | Schollar et al. . |
| 5,540,917 | 7/1996 | Isler et al. . |
| 5,593,971 | 1/1997 | Schollar et al. . |
| 5,629,338 | 5/1997 | Okuda et al. . |
| 5,643,874 | 7/1997 | Bremer et al. . |

FOREIGN PATENT DOCUMENTS

| | | |
|---|---|---|
| 638 317 | 2/1995 | European Pat. Off. . |
| 9834607 A1 | 8/1998 | WIPO . |
| 984630 A1 | 8/1998 | WIPO . |

OTHER PUBLICATIONS

Diaete & Metabolisme 1993, col. 19, p. 547–559.
FDC Reports T&G–1, Oct. 7, 1996.
Fried, M., Digestion 52(2) 82–83 (1992).
Diabetologia 36 (Suppl. 1) Abstract A184, 1993.
Diabetes Care (USA) 19/11 pp. 1311–1315 (1996).
Diabetes Care (USA) 18/8, 1215–1219 (1995).
Prous et al., "Orlistat", Drugs of the Future, vol. 19, No. 11 (1994).
Abstract for JP 09 227 398.
Hollanders et al., "Orlistat Enhances Weight Loss in Obese Patients with Diabetes", American Family Physician, vol. 56, No. 2 (1997).
Deutsche Apotheker Zeitker Zeitung (Dec. 18, 1997) 137/Suppl. (4–8) (Translation not available).
Journal of Clinical Pharmacology 35(5) 521–525, (1995).
26th Annual Meeting of the European Association for the Study of Diabetes, Copenhagen, Denmark, Sep. 10–14, 1990. Diabetologia 33 (Suppl) 1990.
Diabetes Care (1997) 20/11, 1744–1766.
Drugs & Aging 11(5), 1997, 338–351.
Diabetes Front. (1997) 8(3), 374 (Translation not available).
Netherlands Journal of Medicine (1997) 51/3 (96–102).
Abstracts of the 16th International Diabetes Federation Congress, Helsinki, Finland, Jul. 20–25, 1997. Diabetologia 40 (Suppl. 1), 1997.
Drent et al(I) Diabetologica 33 Suppl. A124, 1990.
Drent et al(II) Diabetologica 36 Suppl. I A184, 1993.
Hauptman Am. J. Clin. Nutr. 55 Suppl. I:309S–313S, 1992.
Derewenda et al Trends Biochem Sci 18: 20–23, 1993.
Zhi et al(I) Clin Pharmacol. Ther 56(1): 82–85, 1994.
Zhi et al(II) J. Clinical Pharmacology 35(5): 521–525, 1995.
Zhi et al(III) J. Clinical Pharmacology 35:1103–1108 1995.
Hollandor (I) American Family Physician 56(2):566, Jul. 1999.
Rissanen(I)Int. JL. Obesity 22 Suppl 3 S274–p677, Aug. 1998.
Hollander(II) Diabetes Caro 21(8): 1288–1294, Aug. 1998.
Rissanen(II) Eur. J. Clin. Invest. 28 Suppl 2: 27–30, Sep. 1998.
Williams Int. J. Obesity. 23 Suppl 7 52–54, Jun. 1999.
Bloomgarien Diabetes Care 22(6): 989–995 (Lenoglobin etc) 1999.
Hauner Int. JL Obesity 23 Suppl. 7 512–517, Jun. 1999.
Guerciolini Int. JL. Obesity 21 Suppl. 3S–12–S23, 1997.
James et al. Int. JL. Obesity 21 Suppl 3 S24–S30 120MGTI1997.
Kolley Obes. Res. 5 Suppl 1 215 concem Mexico Nov. 1997 a membe of clinical trios Type II, 1997.

*Primary Examiner*—Shep K. Rose
*Attorney, Agent, or Firm*—George W. Johnston; William H. Epstein; John P. Parise

[57] ABSTRACT

A method for treating or preventing type II diabetes mellitus comprising administering an effective amount of a gastrointestinal lipase inhibitor, such as, tetrahydrolipstatin.

12 Claims, No Drawings

METHOD FOR TREATING TYPE II DIABETES MELLITUS

CROSS REFERENCE TO RELATED APPLICATIONS

This is a continuation of copending application(s) Ser. No. 09/262,564 filed on Mar. 4, 1999 and which is a continuation of Ser. No. 09/003,138 filed on Jan. 6, 1998.

This application claims priority under 35 U.S.C. § 119(e) of Provisional Application(s) Serial No. 60/037,383, filed Feb. 5, 1997.

BACKGROUND OF THE INVENTION

Diabetes mellitus is a condition characterized by an abnormality of glucose utilization and associated with elevation of blood glucose concentration. The most common form of diabetes mellitus is non-insulin dependent diabetes mellitus (NIDDM: Type II). Over 10 million people in the United States alone are affected with type II diabetes mellitus. The initial approach in treating obese patients affected with type II diabetes mellitus is weight reduction. Other types of treatment include oral hypoglycemics and insulin. See, Gregerman, MD, Section 10, Metabolic and Endocrinological Problems, Chapter 72, Diabetes Mellitus, pages 977–989.

SUMMARY OF THE INVENTION

The invention relates to a method of treating type II diabetes mellitus comprising administering to a host in need of such treatment an effective amount of a gastrointestinal lipase inhibitor, preferably tetrahydrolipstatin.

In another aspect the invention relates to a method of preventing type II diabetes mellitus comprising administering to a host an effective amount of a gastrointestinal lipase inhibitor, preferably tetrahydrolipstatin.

DETAILED DESCRIPTION OF THE INVENTION

The invention relates to a method of treating type II diabetes mellitus comprising administering to a host in need of such treatment an effective amount of a gastrointestinal lipase inhibitor, preferably tetrahydrolipstatin.

In another aspect, the invention relates to a method of preventing type II diabetes mellitus comprising administering to a host an effective amount of a gastrointestinal lipase inhibitor, preferably tetrahydrolipstatin.

Tetrahydrolipstatin, also known as orlistat, is a known compound useful for the control or prevention of obesity and hyperlipidemia. See, U.S. Pat. No. 4,598,089, issued Jul. 1, 1986.

Gastrointestinal lipase inhibitors of the invention can be prepared by known methods.

Processes for making tetrahydrolipstatin are set forth in U.S. Pat. No. 4,598,089, issued Jul. 1, 1986; U.S. Pat. No. 4,983,946, issued Jan. 8, 1991; and U.S. Pat. No. 5,245,056, issued Sep. 14, 1993.

It has now surprisingly been found that a gastrointestinal lipase inhibitor, preferably tetrahydrolipstatin, when administered orally is useful in the treatment and prevention of type II diabetes mellitus.

The instant invention comprises treating or preventing type II diabetes mellitus in a subject by orally administering to the subject from 60–720 mg per day of a gastrointestinal lipase inhibitor. Preferably, the gastrointestinal lipase inhibitor is administered in divided doses two to three times per day.

Preferably, the gastrointestinal lipase inhibitor is tetrahydrolipstatin.

Preferred is wherein from 180–360 mg per day of a gastrointestinal lipase inhibitor is administered to a subject, preferably in divided doses two to three times per day.

Particularly preferred is wherein from 180–360 mg per day of a gastrointestinal lipase inhibitor is administered in divided doses three times a day to a subject.

Most preferred is wherein about 360 mg per day of a gastrointestinal lipase inhibitor is administered preferably in divided doses three times a day to a subject.

The subject of the instant invention is preferably an obese or overweight human.

As used herein, the term "obese or overweight human" means a human with a body mass index of 25 or greater.

Generally, it is preferred that the gastrointestinal lipase inhibitor be administered within about two hours of ingestion of a meal containing fat. More preferred is administration of the gastrointestinal lipase inhibitor within about one hour of ingestion of a meal containing fat.

Generally, for preventing type II diabetes mellitus it is preferred that treatment be administered to 1) a human who has a strong family history of type II diabetes mellitus and has obtained a body mass index of 25 or greater; or 2) a human with impaired glucose tolerance who has obtained a body mass index of 25 or greater.

As used herein, the term "strong family history" means a human with at least one first degree relative who has type II diabetes mellitus. Generally, impaired glucose tolerance would be diagnosed by an oral glucose tolerance test.

Tetrahydrolipstatin can be administered in accordance with this invention to humans in conventional oral compositions, such as, tablets, coated tablets, hard and soft gelatin capsules, emulsions or suspensions.

Examples of carriers which can be used for tablets, coated tablets, dragees and hard gelatin capsules are lactose, maize starch or derivatives thereof, talc, stearic acid or its salts and the like. Suitable carriers for soft gelatin capsules are, for example, vegetable oils, waxes, fats, semi-solid and liquid polyols and the like.

Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

The formulations may conveniently be presented in unit dosage form and may be prepared by any methods known in the pharmaceutical art.

Preferably, tetrahydrolipstatin is administered in accordance with this invention in the formulation of Example 1. See, U.S. Provisional Application Serial No. 60/037,384, filed Feb. 5, 1997 and copending application Ser. No. 09/003,137, filed Jan. 6, 1998.

EXAMPLE 1

| Ingredient | Quantity mg/Capsule |
| --- | --- |
| Tetrahydrolipstatin | 120.00 |
| Microcrystalline Cellulose | 93.60 |

-continued

| Ingredient | Quantity mg/Capsule |
|---|---|
| (AVICEL PH-101) | |
| Sodium Starch Glycolate (PRIMOJEL) | 7.20 |
| Sodium Lauryl Sulfate | 7.20 |
| Polyvinylpyrrolidone (Povidone (K-30)) | 12.00 |
| Purified Water* | — |
| Talc | 0.24 |
| Total | 240.24 mg |

*Removed during processing

Procedure:
1. Blend tetrahydrolipstatin, microcrystalline cellulose, and sodium starch glycolate in a suitable mixer.
2. Granulate with a solution of polyvinylpyrrolidone and sodium lauryl sulfate in purified water.
3. Pass the granulation through an extruder and pass the extrudate through a spheronizer to form pellets.
4. Dry the pellets at 30° C.
5. Add talc and mix.
6. Fill into hard gelatin capsules.

EXAMPLE 2

| Ingredient | Quantity mg/Capsule |
|---|---|
| Tetrahydrolipstatin | 60 |
| Microcrystalline Cellulose | 46.8 |
| Sodium Starch Glycolate | 3.6 |
| Sodium Lauryl Sulfate | 3.6 |
| Polyvinylpyrrolidone | 6.0 |
| Purified Water* | — |
| Talc | 0.12 |
| Total | 120.12 mg |

*Removed during processing.

Procedure:
1. Blend tetrahydrolipstatin, microcrystalline cellulose, and sodium starch glycolate in a suitable mixer.
2. Granulate with solution of polyvinyl pyrrolidone and sodium lauryl sulfate in purified water.
3. Pass the granulation through an extruder and pass the extrudate through a spheronizer to form pellets.
4. Dry the pellets at 30° C.
5. Add talc and mix.
6. Fill into hard gelatin capsules.

EXAMPLE 3

| Ingredient | Quantity mg/Capsule | |
|---|---|---|
| Tetrahydrolipstatin | 60 | 120 |
| Lactose | 40 | 80 |
| Microcrystalline Cellulose | 60 | 120 |
| Sodium Lauryl Sulfate | 5.7 | 11.4 |
| Sodium Starch Glycolate | 20 | 40 |
| Polyvinylpyrrolidone | 10 | 20 |
| Purified Water* | — | — |
| Talc | 0.2 | 0.4 |
| Total | 195.9 mg | 391.8 mg |

*Removed during processing.

Procedure:
1. Blend tetrahydrolipstatin, lactose, microcrystalline cellulose and sodium starch glycolate in a suitable mixer.
2. Granulate with a solution of polyvinylpyrollidone and sodium lauryl sulfate in purified water.
3. Pass the granulation through an extruder, and pass the extrudate through a spheronizer to form pellets.
4. Dry the pellets at 30° C.
5. Add talc and mix.
6. Fill into hard gelatin capsules.

EXAMPLE 4

Study of Patients with Non-insulin Dependent Diabetes Mellitus: A one-year double-blind, placebo-controlled study in 321 non-insulin dependent diabetics stabilized on sulfonylureas, was conducted. The results indicate that 30% of patients treated with tetrahydrolipstatin (120 mg, three-times a day) achieved at least a>5% or greater reduction in baseline body weight compared to 13% of the placebo patients ($p<0.001$). Tetrahydrolipstatin also improved glycemic control in these patients as evidenced by statistically significant reductions in hemoglobin Alc levels (0.5% improvement versus placebo, $p<0.001$) and in doses of sulfonylureas. In this study, 43% of the patients treated with tetrahydrolipstatin were able to reduce or discontinue their oral hypoglycemic medications compared to 29% of the patients receiving placebo, $p<0.0\ 1$. Mean levels of fasting glucose remained essentially unchanged compared to baseline in the tetrahydrolipstatin group (−0.02 mmol/L) while there was an increase (+0.54 mmol/L) in the placebo group, $p<0.05$. There were statistically significant improvements in total cholesterol, LDL-cholesterol, LDL/HDL ratio and triglycerides in the group treated with tetrahydrolipstatin compared to placebo.

EXAMPLE 5

Glucose Tolerance in Obese Patients: Two-year studies that included oral glucose tolerance tests were conducted in obese patients whose baseline oral glucose tolerance test (OGTT) status was either normal, impaired or diabetic.

The progression from a normal Oral Glucose Tolerance Test (OGTT) as baseline to a diabetic or impaired OGTT following two years of treatment with tetrahydrolipstatin (n=242) (120 mg administered orally three-times a day) or placebo (n=201) were compared. Following treatment with tetrahydrolipstatin, 0.0% and 6.2% of the patients progressed from normal to diabetic and impaired respectively, compared to 1.5% and 12.4% of the placebo treatment group respectively, $p<0.01$.

In patients found to have an impaired OGTT at baseline, the percent of patients improving to normal or deteriorating to diabetic status following one and two years of treatment with tetrahydrolipstatin compared to placebo are presented below and the difference between treatment groups was significant:

| Baseline OGTT Status Intent-to-treat population | Patients Normal Post-Treatment | Patients Diabetic Post-Treatment |
|---|---|---|
| Impaired | one year of treatment | one year of treatment |
| Placebo n = 48 | 45.8% | 10.4% |
| Tetrahydrolipstatin* n = 115 | 72.2% | 2.6% |
| Impaired | 2 years of treatment | 2 years of treatment |
| Placebo n = 40 | 47.5% | 7.5% |
| Tetrahydrolipstatin** n = 60 | 71.7% | 1.7% |

*p < 0.01 and **p 0.05, Fisher's Exact Test

The subject invention has been described in terms of its preferred embodiments upon reading the present specification, various alternative embodiments will become obvious to the skilled artisan. These variations are to be considered within the scope and spirit of the invention which is only to be limited by the claims that follow and their equivalents.

What is claimed is:

1. A method of treating type II diabetes mellitus by reducing hemoglobin A1c levels, which comprises orally administering to a human subject afflicted with type II diabetes mellitus an amount of a pharmaceutical preparation in unit dosage form, which consists essentially of tetrahydrolipstatin formulated as an oral composition, the amount of tetrahydrolipstatin being effective to reduce hemoglobin A1c levels and in the range of from about 60 to 720 mg of tetrahydrolipstatin per day.

2. The method of claim 1, wherein the pharmaceutical preparation is administered from two to three times per day.

3. The method of claim 2, wherein the pharmaceutical preparation is administered three times per day.

4. The method of claim 1, wherein the pharmaceutical preparation is administered to provide tetrahydrolipstatin at a dose in the range of about 180 to 360 mg per day.

5. The method of claim 4, wherein the pharmaceutical preparation is administered to provide tetrahydrolipstatin at a dose of about 360 mg per day.

6. The method of claim 5, wherein the pharmaceutical preparation is administered from two to three times per day.

7. The method of claim 6, wherein the pharmaceutical preparation is administered three times per day.

8. The method of claim 1, wherein the subject is obese or overweight.

9. The method of claim 1, wherein the subject is not obese or overweight.

10. The method of claim 2, wherein the pharmaceutical preparation is administered within about two hours of ingestion of a meal containing fat.

11. The method of claim 10, wherein the pharmaceutical preparation is administered within about one hour of ingestion of a meal containing fat.

12. The method of claim 6, wherein the pharmaceutical preparation is administered within about two hours of ingestion of a meal containing fat.

* * * * *